United States Patent [19]
Ruzdijic et al.

[11] Patent Number: 5,990,299
[45] Date of Patent: *Nov. 23, 1999

[54] CONTROL OF CD44 GENE EXPRESSION FOR THERAPEUTIC USE

[75] Inventors: Sabera Ruzdijic; Zbigniew Pietrzkowski; Dariusz Cieslak, all of Santa Ana, Calif.

[73] Assignee: ICN Pharmaceuticals, Inc., Costa Mesa, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/514,542

[22] Filed: Aug. 14, 1995

[51] Int. Cl.$^6$ ............................ C07H 21/04; C07H 21/02

[52] U.S. Cl. .......................................... 536/24.5; 536/23.1

[58] Field of Search .................................. 536/23.1, 24.1, 536/24.3, 24.33, 24.5; 514/44

[56] References Cited

PUBLICATIONS

Gura, Science, vol. 278, pp. 1041–1042, Nov. 7, 1997.
Gura, Science, vol. 270, Oct. 27, 1995, pp. 575–577.
Nature Biotechnology, "Antisense '97: A Roundtable on the State of the Industry", vol. 15, Jun. 1997, pp. 519–524.
Sulston et al., Nature, vol. 356, Mar. 5, 1992, pp. 37–41.
Merzak, Abderrahim et al., "CD44 Mediates Human Glioma Cell Adhesion and Invasion in Vitro", Cancer Research, 54, 3988–3992 (Aug. 1, 1994).
Li, Hong et al., "Varian T Cd44 Adhesion Molecules Are Expressed in Human Brain Metastases but Not in Glioblastomas", Cancer Research, 53, 5345–5349 (Nov. 15, 1993).

*Primary Examiner*—David Guzo
*Attorney, Agent, or Firm*—Robert D. Fish; Crockett & Fish

[57] ABSTRACT

Neoplastic cells which over-express CD44, including especially non-small cell lung cancer and melanoma cancer cells, are treated with antisense oligonucleotides to control CD44 expression. Test results show that the claimed oligonucleotides significantly decreases cell growth in a CD44 sequence specific manner of lung cancer or melanoma cells, or both, but are largely non-toxic to normal cells. Examples of dosing in a clinical setting are provided.

4 Claims, 9 Drawing Sheets

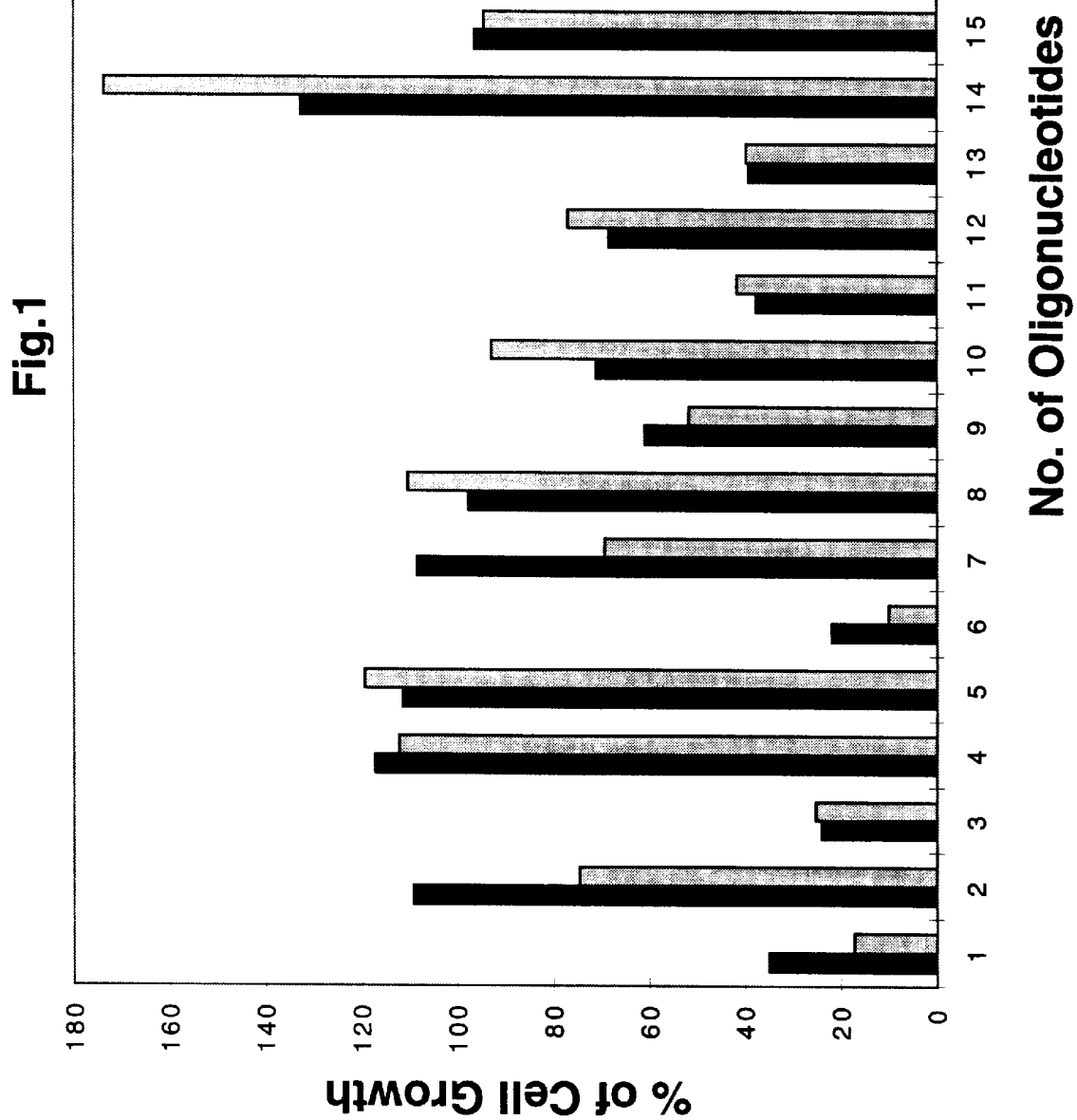

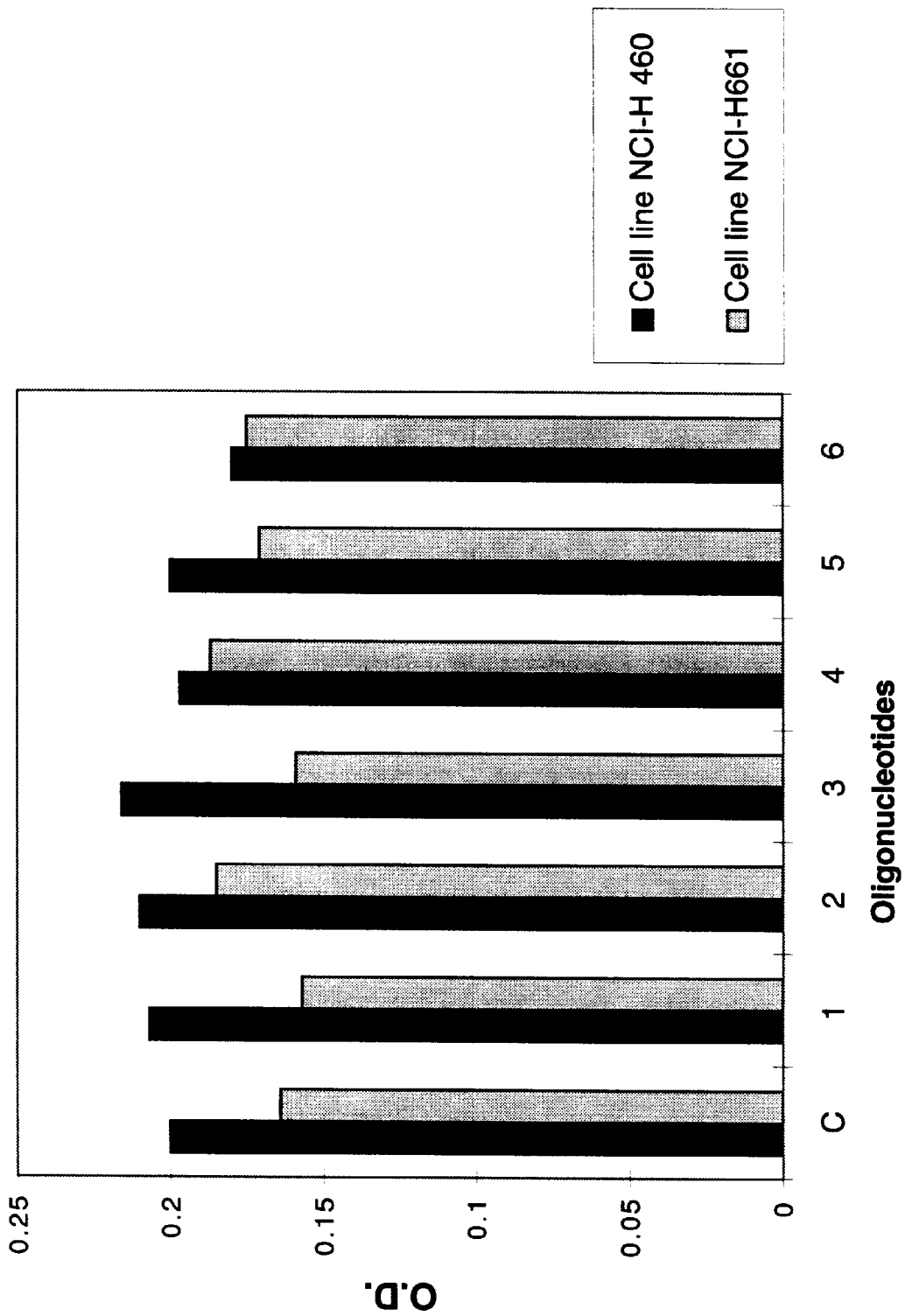

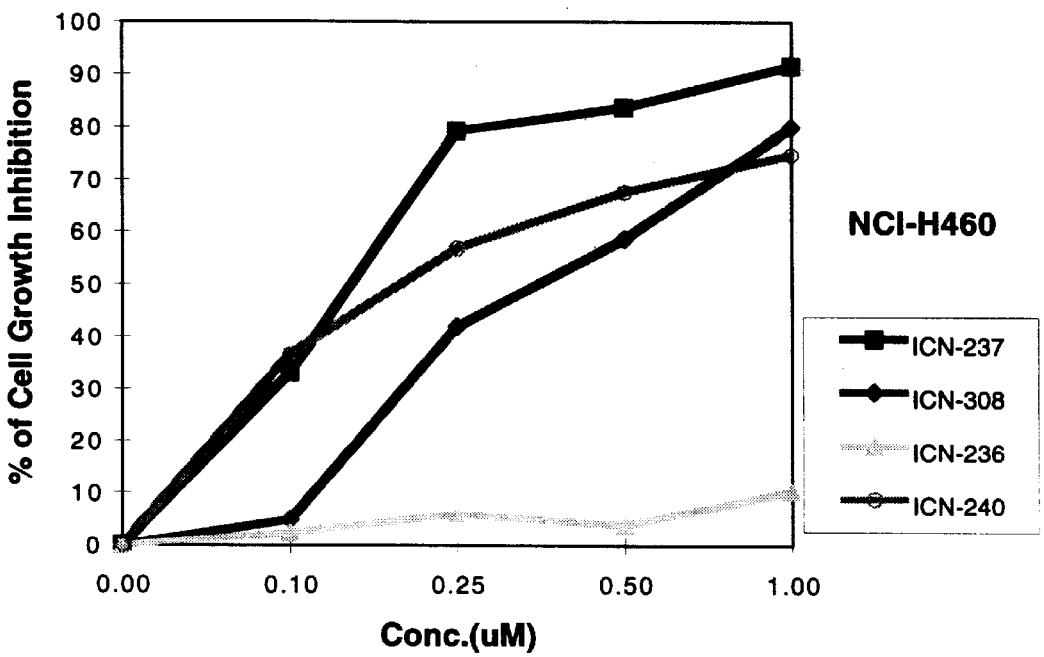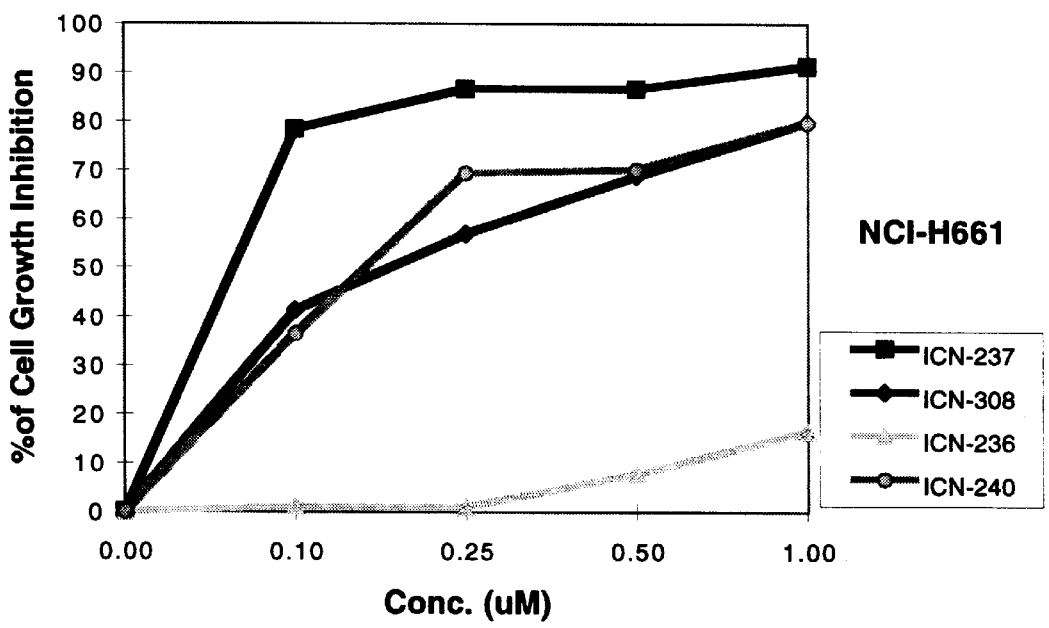

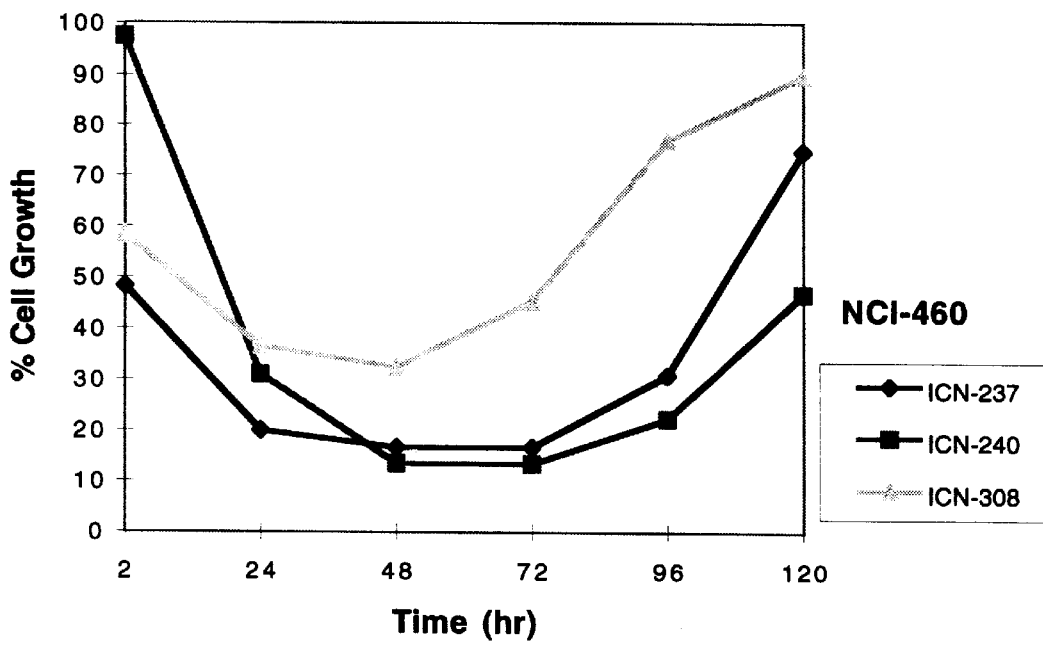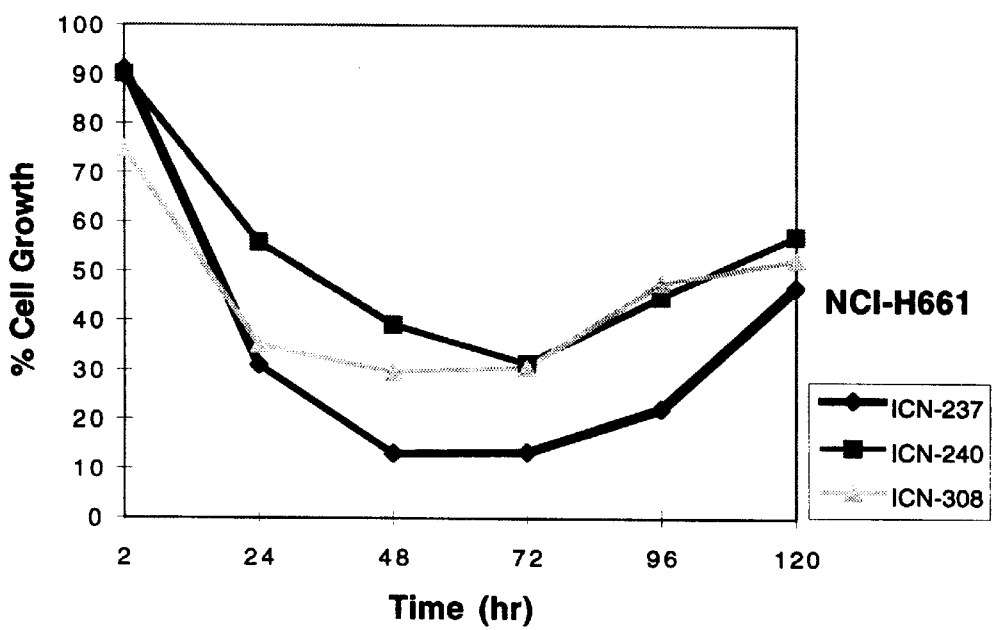

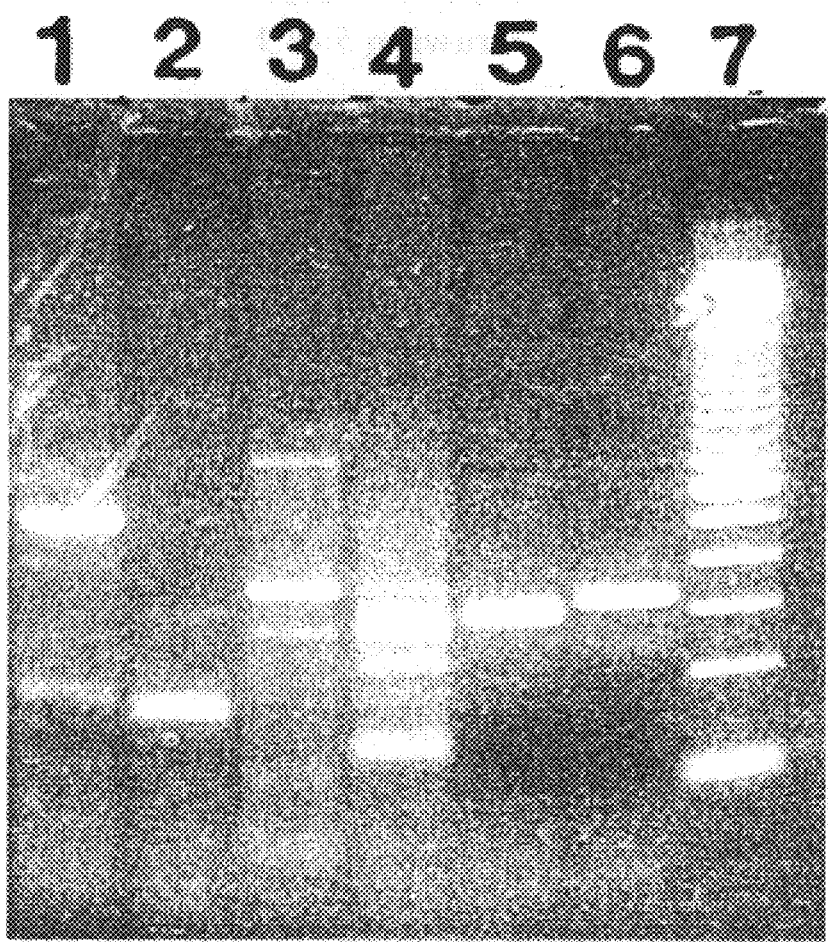

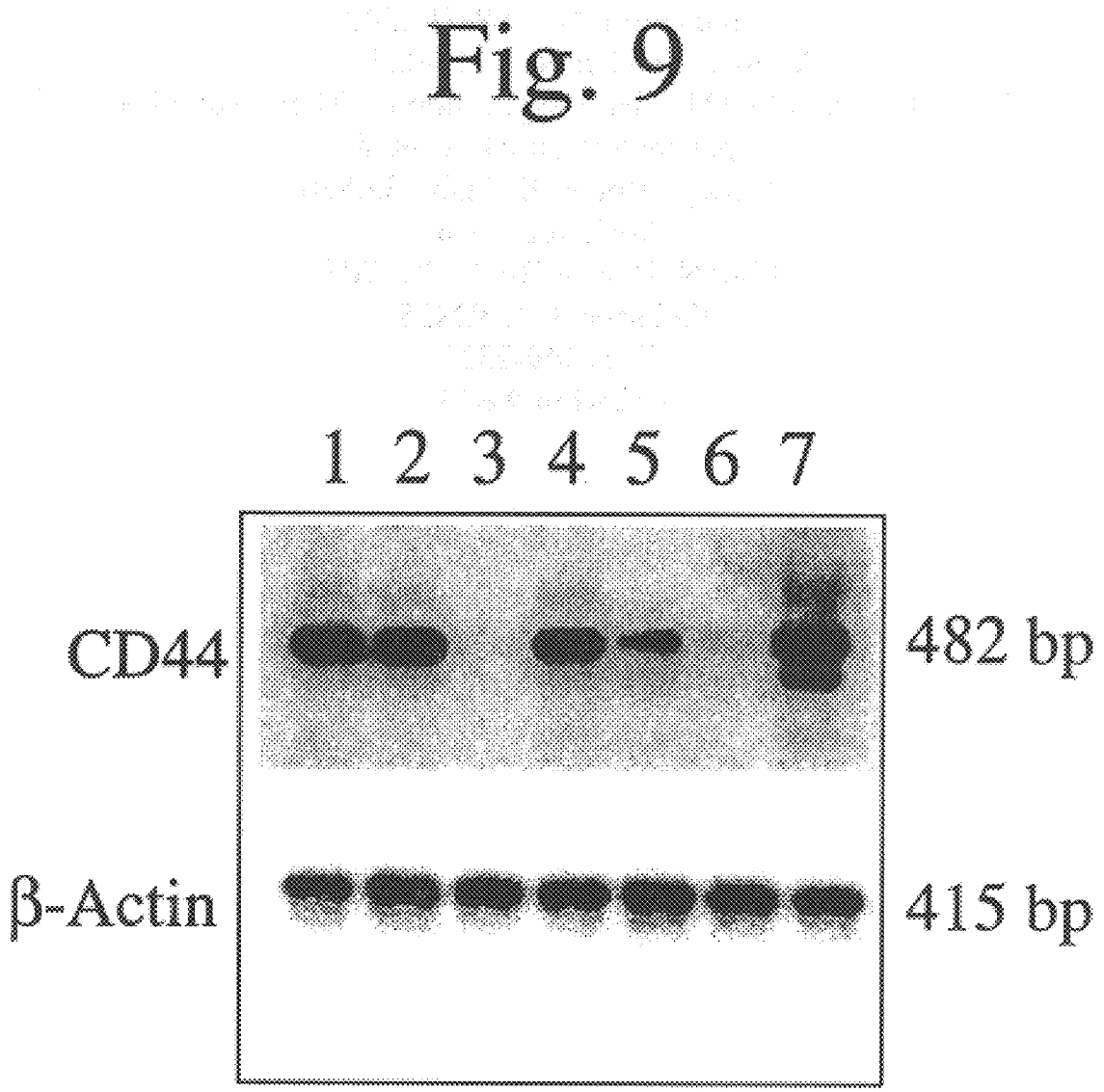

CONTROL OF CD44 GENE EXPRESSION FOR THERAPEUTIC USE

FIELD OF THE INVENTION

The present invention relates to the field of cancer therapy, and more particularly to the use of antisense oligonucleotides to control the expression of CD44.

BACKGROUND OF THE INVENTION

CD44 is a polymorphic family of membrane glycoproteins expressed by many different kinds of cells. CD44 is found, for example, on circulating lymphocytes where it acts as a lymph node homing receptor, and on epithelial cells where it is involved with cell-cell adhesion (1). CD44 is also found in the lungs, on basal cells of the upper bronchi, pulmonary macrophages, alveolar lymphocytes and activated type II alveolar pneuomocytes, where it again functions in cell-cell adhesion (2). CD44 has a high affinity binding site for hyaluronan receptors, and CD44-hyaluronan interactions are used to anchor the cells in place (3).

Within a single cell CD44 may be expressed as two or more variants, presumably depending on the changing needs of the cell. The polymorphic diversity of the variants is generated by alternative splicing of the CD44 mRNA, which occurs when the various coding sequences (exons) of CD44 genes are transcribed (expressed) in different combinations. Protein products of splice variants (isoforms) of CD44 vary widely in size (from 110 kDa to more than 250 kDa) and in function. The extracellular domain of CD44 protein is known to involve cell-cell adhesion and the binding of extracellular matrix components including hyaluronic acid, fibronectin and collagen, while the intracellular domain of CD44 has been associated with ankyrin cytoskeletal proteins critical for CD44-dependent cellular mobility. CD44 has also been found to function in hematopoiesis and in lymphocyte infiltration into general circulation (4, 5, 6). The various functions of CD44 are intriguing because they can be used to explain similar behaviors between activated lymphocytes and metastasizing tumor cells. Both types of cells have relatively high expression of CD44, and both show invasive behavior, cell migration involving reversible adhesive contacts, accumulation and expansion in lymphoid tissue, and release into general circulation (6). The association with lymphoid tissue is especially interesting in that both lymphocytes and metastasizing tumor cells use CD44 variants to bind a specific ligand residing either in the extracellular matrix of the lymph nodes or on the surface of dendritic or other cells of the lymphoid tissue. Moreover, following growth and differentiation in the lymph nodes, both lymphocytes and tumor cells are synchronously released into the efferent lymphatic vessels in the general circulation. The release process requires a complex series of interactions between the lymphocytes and tumor cells, the extracellular matrix component and surrounding cells, and probably involves adhesion receptors, proteolytic enzymes, growth factors and growth factor receptors. These processes may be dependent upon clipping of the CD44 molecules, and specificity in the process may be mediated by tissue-specific ligands interacting with CD44 isoforms. Expression of CD44 in malignant cells is therefore an important factor in primary tumor growth, local invasiveness and metastatic proclivity (7,8,9).

The CD44 gene locus in human genome is on chromosome 11p13 (10). Recently, most of the genomic structure of the human CD44 gene has been established (11). Over a length of about 60 kilobases (kb), at least 20 exons are distributed. Ten of these encode sequences for the standard form of CD44 (exons 1–5 and 16–20). Between exons 5 and 16, at least ten further exons are localized, which are subjected to alternative splicing (exons 6–15). In humans as in other species, the CD44 gene codes a variety of alternatively spliced proteins having different sizes and functions. Several CD44 isoforms have been purified and characterized to date, including an 89–90 kDa glycoprotein referred to as the "standard" or "hematopoietic" isoform (CD44s), and 180 kDa or more glycoproteins referred to as "epithelial" or variant isoforms (CD44v). Isolation and characterization of cDNA clones encoding the standard and epithelial isoforms have shown that the protein sequences are identical except that the epithelial isoforms contain additional sequences of 134 or more amino acids arising from at least ten exons (v1–v10) which code for extra-cellular domain, and the epithelial isoforms are more heavily glycosylated (12, 29). While it is now recognized that the CD44 standard form plays a key role in the control of cell migration, the precise functions of the alternatively spliced CD44 variants, which predominate in most cell types are unknown.

The literature is not conclusive on the issue of whether CD44 expression, either in standard or variant forms, can be generally associated with metastatic potential in human tumors. A 1993 article, for example, points out that such a correlation has never been established (13). On the other hand, it is known that cells which express the highest levels of CD44 variant isoforms tend to be the cells that most often undergo malignant transformation. The uncontrolled growth of these cells coupled with the expression of CD44v isoforms and possibly other adhesion molecules might render them more invasive and metastatic. Also, numerous studies have found associations between malignant transformation or cancer metastasis and the expression of CD44 variant isoforms. For example, a 1994 article gives evidence that certain CD44 variants may help mediate human glioma cell adhesion and invasion (14,15). It has also been shown that uterine cervical carcinomas show strong expression of epitopes encoded by exons v7 and v8, which have not been detected in normal cervical epithelium (16). In another study, specific CD44 variants were shown to be over-expressed at particular stages of colorectal tumor progression, and an unfavorable prognosis has been suggested for colorectal tumors expressing CD44v isoforms previously associated with tumor metastasis (17, 18).

In some studies over-expression of only particular variants has been associated with cancers. For example, expression of variants containing exon v6 sequences occurs in the advanced stages of the development of some tumors, but some CD44 variants without exon v6 sequences appear at the earliest stage of tumorigenesis and in early adenomas. Screening of gastric adenocarcinoma has revealed CD44v expression in all tested specimens, with intestinal type adenocarcinomas expressing variant exons v5 and v6, and diffuse-type adenocarcinomas predominantly expressing only exon v5. Normal stomach mucosa has shown exon v5 expression within the foveolar proliferation zone and on mucoid surface epithelium (19). The same pattern of expression has been confirmed for exon v11 abundantly present in well differentiated intestinal tumors in comparison with diffuse type cancer tissues. Normal gastric mucosas have demonstrated significantly lower expression of exon v11 splice forms. CD44 presence has been associated with tumor recurrence and increased mortality during follow-up averaging 14 months.

There is indication in the literature that over-expression of CD44 has long term clinical significance. In one group of patients with positive expression of exon v6 in 87% of primary breast tumors and 100% auxiliary lymph node metastasis, poor overall survival correlated with the presence of CD44v epitopes (20, 21). Another group found similar results, but suggested that the effect diminishes with time. In a study on gliomas, invasiveness was highly inhibited in two cell lines and completely arrested in five other cell lines by a CD44-specific antisense oligonucleotide which inhibited CD44 expression (15).

To our knowledge, CD44 antisense therapy has never been applied against human lung cancer or melanoma, and it as never even been established that one or more variants of CD44 are associated with either of these types of neoplasm. The problem is exacerbated with respect to lung cancer because there are at least two major types, small cell lung carcinoma (SCLC) and non-small cell lung carcinoma (NSCLC). SCLC comprises approximately one-fourth of the cases, expresses neuroendocrine markers, and generally metastasizes early to lymph nodes, brain, bones, lung and liver. NSCLC comprises the majority of the remaining lung tumor types, and includes adeno-carcinoma, squamous cell carcinoma, and large cell carcinoma. NSCLC is characterized by epithelial-like growth factors and receptors, and is locally invasive. In 1994 Penno and colleagues reported that transcription and translation of CD44 standard form is consistently high among non-small cell tumors and squamous metaplasia of the lung, but is rare in small cell tumors and resting type II pneumocytes (2).

Melanocytes and melanoma cells have been widely studied as a model to investigate changes involved in malignant transformation, including the search for genes expressed in malignant, but not normal, melanocytes. Melanoma cells, unlike normal melanocytes, can proliferate in the absence of exogenous growth factors. This independence apparently reflects the production of growth factor and cytokines for autocrine growth stimulation (22).

Melanoma cells secrete a variety of growth factors including TGF-α, TGF-β, platelet-derived growth factor A and B chains, basic fibroblast growth factor, IL-6, IL-1, granulocyte macrophage colony stimulating factor, and MGSA. These growth factors, expressed either constitutively or subsequent to induction with various cytokines, may contribute to the development of the transformed melanoma phenotype either by acting as autocrine growth factors or by modulating host response to the tumor cells (23, 24).

To produce metastasis, melanoma cells must detach from the primary tumor, invade through host stroma to gain entrance into the circulation, disseminate via the blood stream, and survive to reach distant capillary beds where they must attach, extravasate into the organ parenchyme, and proliferate into secondary growths. The growth of cells in distant sites occurs when the tumor cells produce autocrine growth factors or when the tumor cells respond to paracrine growth factors produced by host cells (22).

Approximately 95% of familial malignant melanomas and 40% of sporadic melanomas arise from precursor lesions. There are three types of melanocytic lesions: congenital, common acquired and dysplastic nevi. Congenital and common acquired nevi represent focal proliferations of normal melanocytes. In contrast, dysplastic nevi consist of a heterogenous population of normal melanocytes and melanocytes showing increased pigmentation, nuclear pleomorphism and mitotic atypia. For this reason, melanocytes of dysplastic nevi are considered to represent precursor lesions of human malignant melanoma. Human melanoma can be classified into three stages: i) melanoma in the radial growth phase; ii) melanoma in the vertical growth phase; and iii) metastatic melanoma. Primary melanoma in the radial and vertical growth phase and metastatic melanomas demonstrate significant biological, biochemical and karyotypic differences from normal human melanocytes and from melanocytic precursor lesions (23).

Human melanoma provides a well-suited model system because cells isolated from different stages of tumor progression can be cultured and studied in the laboratory. The human melanoma Hs294T (ATCC) used in the experiments discussed below was established from lymph node metastasis, and is a highly metastatic melanoma cell line (25). Taken in conjunction with the NSCLC experiments, the Hs294T experiments are thought to be predictive of the general effectiveness of the claimed therapies on neoplasms which over-express CD44.

SUMMARY OF THE INVENTION

The present invention involves the application of antisense oligonucleotides to lung and melanoma cancer cells to control the expression of CD44. The invention also involves oligonucleotides comprising between 13–24 nucleic acid bases, inclusive, capable of reducing CD44 gene expression in lung cancer cells by more than 50%. Some of the preferred antisense oligonucleotides disclosed herein are approximately 95% effective in performing this function, and the effect appears to be sequence specific and nontoxic to normal cells.

BRIEF DESCRIPTION OF THE DRAWINGS

In the drawing, wherein the same reference characters denote similar elements throughout the several views:

FIG. 1 is a bar graph showing the effect of incubation with 22 different oligonucleotides on the cell growth of two lines of lung carcinoma cells (NCI-H460 and NCI-H661). The oligonucleotides which are of interest in this application are the following:

```
Line 1   - ICN-240       (SEQ ID NO:1)

Line 3   - ICN-248       (SEQ ID NO:2)

Line 6   - ICN-237       (SEQ ID NO:3)

Line 11  - ICN-308       (SEQ ID NO:4)

Line 13  - ICN-310       (SEQ ID NO:5)

Line 17  - ICN-314       (SEQ ID NO:6)
```

FIG. 2 is a bar graph showing the cytotoxicity of selected oligonucleotides on cancer cells.

FIGS. 3A and 3B are line graphs showing the effect of varying selected oligonucleotide concentrations on the cell growth of the two lines of lung carcinoma cells.

FIGS. 4A and 4B are line graphs showing the time duration effect of selected oligonucleotides on the cell growth of the two lines of lung carcinoma cells.

FIG. 5 is a photograph of RT-PCR products on agarose gel showing CD44 gene expression after amplification with different pairs of primers in untreated lung cancer cells (NCI-460).

```
Line 1 - P1 (SEQ ID NO:9) + P2 (SEQ ID NO:10)

Line 2 - P3 (SEQ ID NO:11) + P4 (SEQ ID NO:12)

Line 3 - P5 (SEQ ID NO:13) + P6 (SEQ ID NO:14)

Line 4 - P6 (SEQ ID NO:14) + P7 (SEQ ID NO:15)

Line 5 - pHE7

Line 6 - PCNA (proliferating cells nuclear antigen)

Line 7 - 100 bp DNA ladder
```

Figure 6:
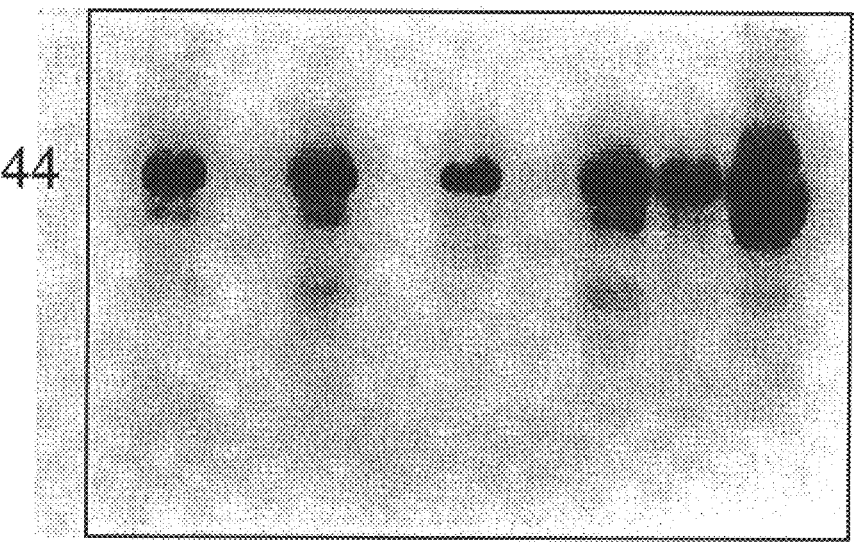

FIG. 6 is an autoradiograph of a Southern blot analysis of RT-PCR products after treatment of human lung cancer cells (NCI-H460) with antisense, sense and random sequences.

| | | |
|---|---|---|
| Unt. | - untreated cells | |
| Line 1 | - ICN-237 | (SEQ ID NO:3) |
| Line 2 | - ICN-236 | (SEQ ID NO:7) |
| Line 3 | - ICN-240 | (SEQ ID NO:1) |
| Line 4 | - ICN-248 | (SEQ ID NO:2) |
| Line 5 | - ICN-308 | (SEQ ID NO:4) |
| Line 6 | - ICN-310 | (SEQ ID NO:5) |
| Line 7 | - ICN-314 | (SEQ ID NO:6) |
| Line 8 | - ICN-88 | (SEQ ID NO:8) |

Figure 7:
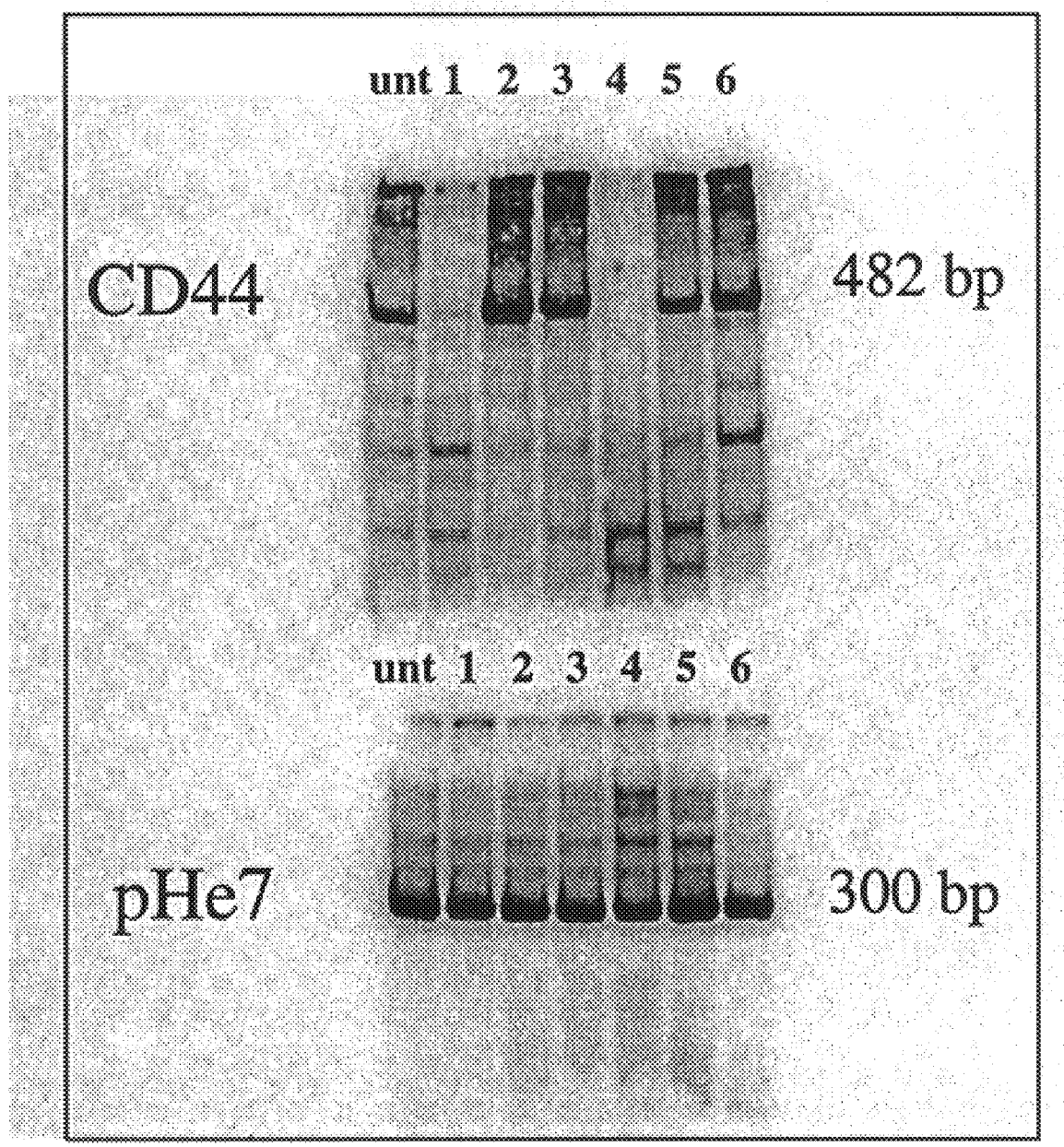

FIG. 7 is fluororadiograph of "hot" RT-PCR products after treatment of lung cancer cells (NCI-H460) with antisense, sense and random sequences, using pHE7 as an internal control.

| | | |
|---|---|---|
| Unt. | - untreated cells | |
| Line 1 | - ICN-308 | (SEQ ID NO:4) |
| Line 2 | - ICN-248 | (SEQ ID NO:2) |
| Line 3 | - ICN-236 | (SEQ ID NO:7) |
| Line 4 | - ICN-240 | (SEQ ID NO:1) |
| Line 5 | - ICN-310 | (SEQ ID NO:5) |
| Line 6 | - ICN-88 | (SEQ ID NO:8) |

Figure 8:
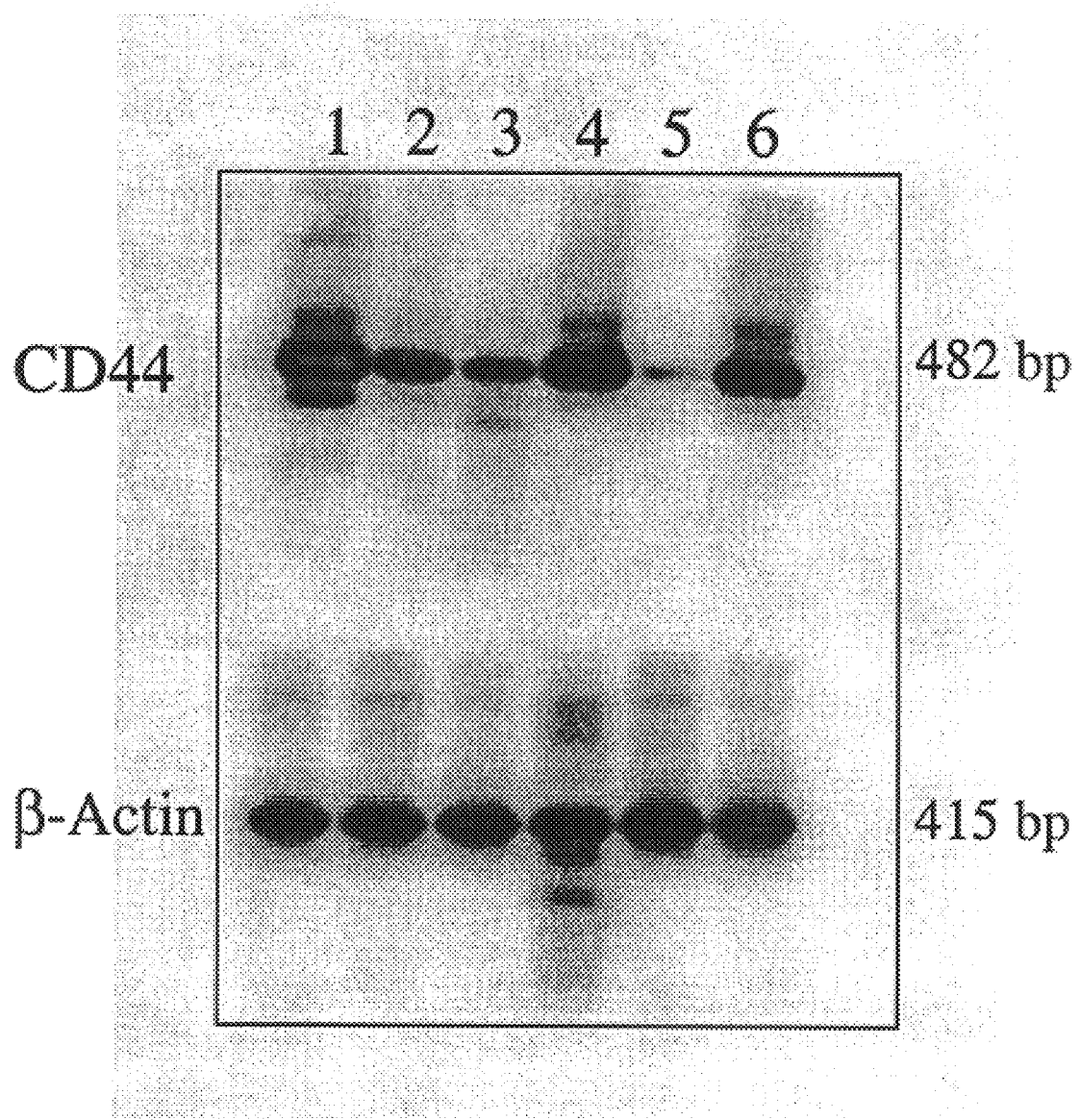

FIG. 8 is an autoradiograph of a Southern blot analysis of RT-PCR products after treatment of lung cancer cells (NCI-H661) with antisense/sense and random sequences, using β-actin as an internal control.[7]

| | | |
|---|---|---|
| Line 1 | - untreated cells | |
| Line 2 | - ICN-237 | (SEQ ID NO:3) |
| Line 3 | - ICN-240 | (SEQ ID NO:1) |
| Line 4 | - ICN-236 | (SEQ ID NO:7) |
| Line 5 | - ICN-308 | (SEQ ID NO:4) |
| Line 6 | - ICN-88 | (SEQ ID NO:8) |

FIG. 9 is an autoradiograph of a Southern blot analysis of RT-PCR products after treatment of melanoma cancer cells (Hs 294T) with antisense, sense and random sequences, using β-actin as an internal control.

| | | |
|---|---|---|
| Line 1 | - untreated | |
| Line 2 | - ICN-237 | (SEQ ID NO:3) |
| Line 3 | - ICN-240 | (SEQ ID NO:1) |
| Line 4 | - ICN-236 | (SEQ ID NO:7) |
| Line 5 | - ICN-308 | (SEQ ID NO:4) |
| Line 6 | - ICN-248 | (SEQ ID NO:2) |
| Line 7 | - ICN-88 | (SEQ ID NO:8) |

DETAILED DESCRIPTION

The discussion below describes the production of various oligonucleotide sequences, and the testing of the sequences for their effectiveness against lung and/or melanoma cancer cells. The antisense and sense oligonucleotides for human CD44 cDNA were fragments of those designated in the sequences published by Stamenkovic et al. (26). Altogether, twenty-two-nucleotides were synthesized and tested, from which the following were selected for further evaluation:

| REF. NO. SEQUENCE | POSITION (BP IN CD44 CODING SEQUENCE) | SEQ ID NO |
|---|---|---|
| Antisense Oligonucleotides | | |
| ICN-240  5' ATTCGAAATG AAACAA | 1620 | SEQ ID NO:1 |
| ICN-248  5' TTTATCTTCT TCCAAGGCGA AGC | 991 | SEQ ID NO:2 |
| ICN-237  5' TTTATCTTCT TCCAAG | 991 | SEQ ID NO:3 |
| ICN-308  5' TTCCTCCCAG GAC | 2038 | SEQ ID NO:4 |
| ICN-310  5' AAATTTCCTC CCAG | 2038 | SEQ ID NO:5 |
| ICN-314  5' GGCAGGTTAT ATTCA | 250 | SEQ ID NO:6 |
| Sense Oligonucleotide | | |
| ICN-236  5' ATTTGAATAT AACCTGGCGA AGC | 246 | SEQ ID NO:7 |
| Random Oligonucleotide | | |
| ICN-88   5' TGCCAGACTA TTGTCCCA | n/a | SEQ ID NO:8 |

All tested sequences were synthesized on an automated DNA synthesizer (Applied Biosystems model 394) as phosphodiester oligonucleotides using standard phosphoroamidite chemistry. The resulting oligonucleotides were purified by HPLC using a reverse phase semiprep C8 column (ABI) with linear gradient of 5% acetonitrile in 0.1 M triethylammonium acetate and acetonitrile. The purity of the products was checked by HPLC using an analytical C18 column (Beckman).

Testing of the twenty-two oligonucleotide sequences was carried out on large cell lung carcinoma lines NCI-H460 and NCI-H661 and melanoma cancer cells Hs294T from the American Type Culture Collection. The cells were routinely propagated in culture in a humidified incubator at 37° C. in 5% $CO_2$/95% air at atmospheric pressure. Both cell lines were grown as adherent cultures in 90% RPMI 1640, supplemented with 10% fetal bovine serum. Cells were seeded in 96-well microtiter plates at 2,000 cells per well, and subsequently treated with various concentrations (0.1, 0.25, 0.5, 1.0 $\mu$M) of the antisense and sense oligonucleotides described more fully below. After 72 h of culture, all cells were pulsed with 1 $\mu$Ci/ml of [$^3$H] thymidine, cultured for an additional 2 h, harvested with an automatic Harvester 96 (Tomtec), and [$^3$H] thymidine incorporation determined in a $\mu$-counter. To assure accuracy of the results, all cultures were performed in triplicate and repeated at least three times.

In the preliminary lung cancer screening, samples of the lung carcinoma cell lines NCI-H460 and NCI-H661 were incubated in the presence of 0.5 $\mu$M of each of the oligonucleotides for 72 hr before being tested for DNA inhibition. FIG. 1 shows the results of the screening, in which each of the vertical lines (1–22) represents the effectiveness of a particular oligonucleotide in arresting cell growth. Six of the antisense oligonucleotides, Line 1-ICN-240 (SEQ ID NO:1); Line 3-ICN-248 (SEQ ID NO:2); Line 6-ICN-237 (SEQ ID NO:3); Line 11-ICN-308 (SEQ ID NO:4); Line 13-ICN-310 (SEQ ID NO:5); and Line 17-ICN-314 (SEQ ID NO:6), almost completely arrested cell growth in lung carcinoma, whereas the rest of the tested oligonucleotides had minimal effect on cell growth.

FIG. 2 shows the results of testing these six oligonucleotides (from FIG. 1) for cytotoxicity on both lung cancer cell lines using neutral red uptake (Clonetics, San Diego). Each of the oligonucleotides registered in the range of untreated cells, indicating that they are not cytotoxic during treatment.

FIGS. 3A and 3B show the results of testing three antisense ICN-240 (SEQ ID NO:1); ICN-237 (SEQ ID NO:3); ICN-308 (SEQ ID NO:4) and one sense ICN-236 (SEQ ID NO:7) oligonucleotides for dose response. In these experiments, samples of the two lung cancer cells were treated with different concentrations (0.1, 0.25, 0.5, 1.0 $\mu$M) of the oligonucleotides for 72 hr. All three of the antisense oligonucleotides showed increasing inhibition of cell growth with increasing concentrations of oligonucleotide, with cell growth begin inhibited from 55 to 95% at concentrations between 0.25 and 0.5 $\mu$M. Increasing concentration of the sense oligonucleotide ICN-236 (SEQ ID NO:7) did not affect cell growth.

FIGS. 4A and 4B show the results of testing antisense oligonucleotides ICN-237 (SEQ ID NO:3), ICN-240 (SEQ ID NO:1), and ICN-308 (SEQ ID NO:4) on the two lines of lung cancer cells over a period of six days. As is readily seen, the highest percentage (20–45%) of cell growth inhibition occurred between 24 and 48 hours for all three selected antisense oligonucleotides, and the effect was essentially nullified by 72–120 hours.

To confirm sequence specificity we examined various oligonucleotides, ICN-88 (SEQ ID NO:8); ICN-236 (SEQ ID NO:7); ICN-237 (SEQ ID NO:3); ICN-240 (SEQ ID NO:1); ICN-248 (SEQ ID NO:2); and ICN-308 (SEQ ID NO:4) using RT-PCR. In that procedure total cellular RNA extraction from both lung cancer cell lines and melanomas was isolated by the guanidine isothiocyanate method (GlassMAX RNA Microisolation Spin Cartridge System—Gibco BRL), and first strand cDNA synthesis was carried out using 0.5 $\mu$g total RNA, oligo(dT) primer and M-MLV reverse transcriptase according to the instructions of the manufacturer (Perkin Elmer Cetus). We then choose primers that specifically anneal to certain portions of the CD44 gene to amplify portions of the gene coding for specific CD44 proteins. The primers and DNA probe we used for human CD44 cDNA were those designated in the sequences published by Stamenkovic et al. (1989) (26) as follows:

| PRIMERS | SEQUENCES 5'-3' | | POSITION (bp) | SEQ ID NO |
|---|---|---|---|---|
| P-1 | GACACATATT GCTTCAATGC | TTCAGC | 520 | SEQ ID NO:9 |
| P-2 | GATGCCAAGA TGATCAGCCA | TTCTGGAAT | 920 | SEQ ID NO:10 |
| P-3 | AGCAGAGTAA TTCTCAGAG | | 947 | SEQ ID NO:11 |
| P-4 | CTGATAAGGA ACGATTGACA | | 1,221 | SEQ ID NO:12 |
| P-5 | GAGACCAAGA CACATTCCAC | C CCA G | 1.241 | SEQ ID NO:13 |
| P-6 | ACTCCTTGTT CACCAAATGCA | | 1,561 | SEQ ID NO:14 |
| P-7 | ACACCTTGTT CACCAAATGCA | | 192 | SEQ ID NO:15 |

PCR primers P-1(SEQ ID NO:9) and P-2(SEQ ID NO:10) are equivalent to primers used by Matsamura and Tarin (27), and are designed to anneal the standard portion of the CD44. These primers yield a PCR fragment of 480 bp in samples expressing standard CD44, a fragment of 878 bp in samples expressing the epithelial form of CD44, and fragments producing several different bands in samples containing alternatively spliced transcripts. The cDNA products (10% of the total in each case) were then used as templates for PCR in a reaction mixture that comprised 1× Taq buffer, $MgCl_2$ (1.5 mM), dNTP (500 $\mu$M), the appropriate 5' and 3' primers, and Taq I polymerase (50 units/ml). The cycle parameters in all cases were 55° C. for 8 min; 94° C. for 1 min; 55° C. for 1 min; and 72° C. for 2 min; (35 cycles) followed by 72° C. for 8 min.

To verify quality and quantity, cDNA was also amplified by PCR with ribosomal gene(pHE7),[31] sense primer 5' CTTCGAAAGG CAAGGAGGAA(SEQ ID NO:16)and antisense primer 5' TGGCTCTACA ATCCTCAGCA(SEQ ID NO:17), primers or β-actin sense primer 5' CAGCCAT-GTA CGTTGCTATC CAG (SEQ ID NO:18), and antisense primer 5' GTTTCGTGGA TGCCACAGGA C (SEQ ID NO:19), as internal controls. This resulted in the generation of the 300 bp fragment for ribosomal gene or 450 bp for β-actin. 10 ul of each PCR product was electrophoresed in 1.5% agarose gel and then transferred to positively charged nylon membranes (Boehringer Mannheim) for hybridization with CD44 oligonucleotide probe 5' CCTGAAGAAG ATTGT ACATC AGTCACAGAC (SEQ ID NO:20). The probe was radiolabelled with g-$^{32}$P-ATP at the 5' end in the presence of $T_4$ polynucleotide kinase. Prehybridization and hybridization were performed in Rapid Hybridization Buffer (Amersham) at 42° C. for 90 min. The filter was then washed twice in 5×SSC, 1×SSC with 0.1% SDS at 42° C. sequentially for 15 min each, and analyzed using a Molecular Imager (GS-250, Bio-Rad).

To confirm expression of CD44 molecules we first examined untreated cells from lung carcinoma NCI-H460 using combinations of primers designed to amplify different coding regions of CD44 the gene (26). In that procedure, RNA samples were prepared from approximately 5×10$^5$ cells, and analyzed by RT-PCR under the same conditions as described above. As expected, PCR amplification using the primers P-1 (SEQ ID NO:9) and P-2 (SEQ ID NO:10) generated 480 bp fragments from RNA for the standard CD44 isoform (FIG. 5, Line 1). In contrast, other fragments of CD44 having significantly different molecular sizes were expressed by different combinations of other primers (FIG. 5, line 2-P3 SEQ ID NO:11)+P4 (SEQ ID NO:12); Line 3-P5 (SEQ ID NO:13)+P6 SEQ ID NO:14); and Line 4 -P6(SEQ ID NO:14)+P7(SEQ ID NO:15)).

To address the question of how one of the selected antisense oligonucleotides can inhibit CD44 mRNA expression, we then examined CD44 expression using a combination of RT-PCR and Southern blot hybridization. Primers P-1(SEQ ID NO:9) and P-2 (SEQ ID NO:10) used for RT-PCR were derived from exons (1–5 and 16–20) encoding "standard" isoform sequences adjacent to the variant insert. Again, as expected from the published data (30) and our previous results summarized in FIG. 5, the amplification with primers P-1 (SEQ ID NO:9) and P-2 (SEQ ID NO:10) generated only CD44 "standard" isoform. RNA samples were then prepared from both lines of lung cancer cells, some of which had not been treated with antisense oligonucleotides, and some of which had been treated with antisense oligonucleotides (0.5 μM for 2 h). We tested our six selected antisense oligonucleotides, and one sense and one random oligonucleotide as controls (FIG. 6). After RT-PCR and Southern blotting analysis we found that three of the antisense oligonucleotides consistently exhibited superior inhibition of the CD44 mRNA expression in NCI-H460 cell lines (see FIG. 6, line 1-ICN-237 (SEQ ID NO:3) ; line 3 -ICN-240 (SEQ ID NO:1) and line 5 -ICN-308 (SEQ ID NO:4). A similar effect of mRNA inhibition was found in the NCI-H661 (FIG. 8, Line 2-ICN-237 (SEQ ID NO:3); Line 3-ICN-240 (SEQ ID NO:1); and Line 5-ICN-308 (SEQ ID NO:4)). In contrast, CD44 expression was positive in untreated cells (FIG. 8, line 1), or in the cells treated either with sense or random oligonucleotides (see FIG. 8, Line 4-ICN-236 (SEQ ID NO:7); and Line 6-ICN-88 (SEQ ID NO:8)).

Quantitative determination of the decrease in CD44 mRNA molecules following treatment of lung carcinoma cells with antisense oligonucleotides (FIG. 7) was performed using "hot" PCR. That procedure involved essentially the same protocols described above, except that one of the deoxynucleotides in the mix was radiolabeled during PCR amplification, and final PCR products were labeled. The results were that at 0.5 μM concentration of antisense oligonucleotides, the CD44 mRNA expression was decreased by 79–94 % after 2 h treatment, as determined densitometrically. (FIG. 7, Line 1-ICN-308 (SEQ ID NO:4); and Line 4 -ICN-240 (SEQ ID NO:1)). No similar effect was observed with either the sense or random oligonucleotides (FIG. 7, Line 3 -ICN-236 (SEQ ID NO:7); and Line 6 -ICN-88 (SEQ ID NO:8)), or with two other antisense oligonucleotides (FIG. 7, Line 2 -ICN-248 (SEQ ID NO:2); and Line 5 -ICN-310 (SEQ ID NO:5)). Furthermore, none of the oligonucleotides tested affected the ribosomal RNA levels (pHE7), thus demonstrating selectivity for the targeted CD44 mRNA.

FIG. 9 is a Southern blot analysis similar to that of FIG. 6. Here, however, samples of melanoma cancer cells (Hs294T) were incubated with four antisense. Here, however, samples of melanoma cancer cells (Hs294T) were incubated with four antisense, ICN-237 (SEQ ID NO:3), ICN-240 (SEQ ID NO:1), ICN-310 (SEQ ID NO:5), and ICN-248 (SEQ ID NO:2), one sense, ICN-236 (SEQ ID NO:7) and one random, ICN-88 (SEQ ID NO:8) oligonucleotides. After RT-PCR and Southern blotting analysis we found that two of the antisense oligonucleotides inhibited CD44 mRNA expression with a very high effectiveness, 91% for Line 3-ICN-240 (SEQ ID NO:1) and 84% for Line 5-ICN 248 (SEQ ID NO:6), and the remaining antisense, line 5-ICN-308 (SEQ ID NO:4) shoeed an effectiveness of about 54%. Line 4-ICN-236 (SEQ ID NO:4), and random, line 7-ICN-88 (SEQ ID NO:8) oligonucleotides, along with the untreated cells, Line 1, showed no effect. β-actin was used as the internal control.

Delivery of oligonucleotides as described herein is well known in the art for a wide range of animals, including mammals, further, the oligonucleotides of the present invention can be administered in a "naked" form, encapsulated, in association with vesicles, liposomes, beads, microspheres, as conjugates, and as an aerosol directly to the lung, using for example ICN Biomedicals product no. SPAG 2. Thus, oligonucleotides of the present invention can be administered substantially by all known routes of administration for oligonucleotides, using all accepted modifications to produce nucleotide analogs and prodrugs, and including all appropriate binders and excipients, dosage forms and treatment regimens.

At present the most preferred administration of the oligonucleotides of the present invention comprises intravenous administration of between about 0.1 and 10 mg of oligonucleotide per kg of body weight of the patient, 1–2 times per day for approximately 40 days. This regimen is based upon the observed half-life for similar oligonucleotides in vivo of up to several hours, along with the observation that the effect upon protein synthesis may last up to 48 or 72 hours. The specific treatment regimen given to any individual patient will, of course, depend upon the experience of the clinician in weighing the disease involved, the health and responsiveness of the patient, side effects, and many other factors as is well known among such clinicians. For example, greater of lesser dosage levels, and treatment regimens covering greater or lesser periods of time would be dependent upon the judgment of the attending clinician, and may include periods of rest during which treatment with the oligonucleotide is temporarily halted. Treatment may also be combined with other anticancer and palliative treatments as appropriate. Progression/remission of the disease being treated may be determined by following tumor size, extent of metastasis and other factors through radiological analysis and other means known in the art, and the existence and extent of side effects may be determined by following functioning of the liver and/or kidneys, and by following the blood circulation as for example through the use of EKG, which again are well known in the art.

Thus, antisense oligonucleotides effective in controlling CD44 expression in cancer cells which overproduce CD44, and in particular non-small cell lung cancer and melanoma cells, have been disclosed. Procedures for using these oligonucleotides in clinical practice have also been disclosed. While specific embodiments and applications have been shown and described, it would be apparent to those skilled in the art that additional modifications are possible without departing from the inventive concepts herein. The invention, therefore, is not to be restricted except in the spirit of the appended claims.

REFERENCES:

1. Haynes F. B., Telen, J. M., Hale, P. L. Denning M. S. CD44-A molecule involved in leukocyte adherence and T-cell activation. Immunology Today, 1989, 10: 423–4282.
2. Penno M B, August J T, Baylin S B, Mabry M, Linnoila R I, Lee V S, Croteau D, Yang X L and Rosada C: Expression of CD44 in Human Lung Tumors. Cancer Res., 1994, 54, 1381–1387.
3. Lesley J, Hyman R and Kincade P W: CD44 and its Interaction with Extracellular Matrix. Adv. Immunol. 1994, 54: 271–335.
4. Sherman L., Sleeman J., Herrlich P., Ponta H., Hyaluronate receptors: key players in growth, differentiation, migration and tumor progression. Current Opinion in Cell Biology, 1994, 6: 726–733.
5. Gunthert U. CD44: A multitude of isoforms with diverse functions. Current Topics in Microbiology and Immunology, 1993, 184: 47–55.
6. Herrlich P., Zoller M., Pals T., Ponta H., CD44 splice variants: metastases meet lymphocytes. Immunol. Today, 1993, 14: 395–399.
7. Salles G, Zain M, Wei-meng J, Boussiotis V A and Shipp A: Alternatively Spliced CD44 Transcripts in Diffuse Large-Cell Lymphomas: Characterization and Comparison with Normal Activated B Cells and Epithelial Malignancies. Blood, 1993, 82: 3539–3547.
8. Koopman G, Heider K H, Horst E, Adolf G R, van der Berg F, Ponta H, Herrlich P and Pals S T: Activated Human Lymphocytes and Aggressive Non-Hodgkin's Lymphomas Express a Homologue of the Rat Metastasis-associated Variant of CD44. J. Exp. Med., 1993, 177: 897–904.
9. Bartolazzi A, Peach R, Aruffo A, Stamenkovic I: Interaction Between CD44 and Hyaluronate is Directly Implicated in the Regulation of Tumor Development. J. Exp. Med., 1994, 180: 53–66.
10. Goodfellow P N, Banting G, Wiles M V, Tunnacliffe A, Parkar M, Solomon E, Dalchau R, Fabre J W: The Gene, MIC4, which Controls Expression of the Antigen Defined by Monoclonal Antibody F10.44.2, is on Human Chromosome 11. Eur. J. Immunol., 1982, 12: 659–663.
11. Screaton G R, Bell M V, Jackson D G, Cornelis F B, Gerth U and Bell J I, Genomic Structure of DNA Encoding the Lymphocyte Homing Receptor CD44 Reveals at Least 12 Alternatively Spliced Exons. Proc. Natl. Acad. Sci, USA, 1992, 89: 12160–12164.
12. Aruffo A, Stamenkovic I, Melnick M, Underhill C B and Seed B: CD44 is the Principal Cell Surface Receptor for Hyaluronate. Cell, 1990, 61: 1303–1313.
13. Seiter S, Arch R, Reber S, Komitowski D, Hofmann M, Ponta H, Herrlich P, Matzku S and Zoller M: Prevention of Tumor Metastasis Formation by Anti-Variant CD44. J. Exp. Med., 1993, 177: 443–455.
14. Li H, Hamou M F, Tribolet N, Jaufeerally R, Hofmann M, Diserens A C and Meir E G: Variant CD44 Adhesion Molecules are Express in Human Brain Metastases but not in Glioblastomas. Cancer Res., 1993, 53: 5345–5349.
15. Merzak A, Koocheckpour S and Pilkington G J: CD44 Mediates Human Glioma Cell Adhesion and Invasion in vitro. Cancer Res., 1994, 54: 3988–3992.
16. Dall P, Heider K H, Hekele A, von Minckwitz G, Kaufmann M, Ponta H and Herrlich P: Surface Protein Expression and Messenger RNA-splicing Analysis of CD44 in Uterine Cervical Epithelium. Cancer Res., 1994, 54: 3337–3341.
17. Wielenga V J M, Heider K H, Offerhaus J A, Gunther R A, van der Berg F M, Ponta H, Herrlich P and Pals S T: Expression of CD44 Variant Proteins in Human Colorectal Cancer is related to Tumor Progression. Cancer Res., 1993, 53: 4754–4756.
18. Finn L, Dougherty G, Finley G, Meisler A, Becich M and Cooper D L: Alternative Splicing of CD44 pre-mRNA in Human Colorectal Tumors. Biochem. Biophy. Res. Commun., 1994, 200: 1015–1022.
19. Heider K H, Dammrich J, Skroch-Angel P, Muller-Hermelink H K, Vollmers H P, Herrlich P and Ponta H: Differential Expression of CD44 Splice Variants in Intestinal-and Diffuse-Type Human Gastric Carcinomas and Normal Gastric Mucosa. Cancer Res., 1993, 53: 4197–4203.
20. Joensuu H, Klemi P J, Toikkanen S and Jalkanen S: Glyco-protein CD44 Expression and its Association with Survival in Breast Cancer. Amer. J. Pathol., 1993, 143: 867–874.
21. Kaufmann M, Heider K H, Sinn H P, von Minckwitz G, Ponta H, Herrlich P: CD44 Variant Exon Epitopes in Primary Breast Cancer and Length of Survival. Lancet, 1995, 345: 615–619.
22. Guo Y, Ma J, Wang J, Che X, Narula J, Bigby M, Wu M and Sy M, Inhibition of Human Melanoma Growth and Metastasis in Vivo by Anti-CD44 Monolclonal Antibody. Cancer Res., 1994, 54: 1561–1565.
23. Aaronson SA, Growth factor and cancer. Science, 254: 1146–1153, 1991.
24. Rodeck U, Growth factor idenpendence and growth factor regulatory pathways in human melanoma development. Cancer and Metastasis Rev., 12:219–226, 1993.
25. Birch M, Mitchell S and Hart I R: Isolation and Characterization of Human Melanoma Cell Variants Expressing High and Low Levels of CD44. Cancer Res., 1991, 51, 6660–6667.
26. Stamenkovic I, Aruffo A, Amiot M, Seed B,: The hemato-poietic and epithelial forms of CD44 are distinct polypeptides with different adhesion potentials for hyaluronate-bearing cells. The EMBO Journal, 1991, 10: 343–348.
27. Matsumura Y, Tarin, Significance of CD44 gene products for cancer diagnosis and disease evaluation. The Lancet, 1992, 340: 1053–1058.
28. Kao H T and Nevins JR, Mol. Cell. Biol. 1983, 2058–206.
29. Iuima S N, Hamada H, Reddy P and Kakunaga T, Molecular structure of the human cytoplasmic β-actin gene: Inerspecies homology of sequences in the introns. Proc. Nat. Acad. Sci. USA, 1985, 82: 6133–6137.

What is claimed is:

1. An oligonucleotide that reduces CD44 gene expression in lung cancer cells by more than 50%.

2. An oligonucleotide according to claim 1 comprising between 13 and 24 nucleic acid bases, inclusive.

3. An oligonucleotide according to claim 1 comprising a DNA molecule.

4. An oligonucleotide according to claim 1 having the following sequence: 5' ATT CGA AAT GAA ACA A (SEQ ID NO:1) wherein said oligonucleotide hybridizes to a CD44 gene.

* * * * *

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
       (A) LENGTH: 16 base pairs
       (B) TYPE: nucleic acid
       (C) STRANDEDNESS: unknown
       (D) TOPOLOGY: unknown (ii) MOLECULE TYPE: DNA (iii) HYPOTHETICAL: no (iv) ANTI-SENSE: yes (v) FRAGMENT TYPE:

(vi) ORIGINAL SOURCE:

(vii) IMMEDIATE SOURCE:

(viii) POSITION IN GENOME: CD44 1620

(ix) FEATURE:

(x) PUBLICATION INFORMATION:

(xi) SEQUENCE DESCRIPTION: SEQ ID NO:1:

ATTCGAAATG AAACAA                                                  16

(2) INFORMATION FOR SEQ ID NO:2:

(i) SEQUENCE CHARACTERISTICS:
       (A) LENGTH: 23 base pairs
       (B) TYPE: nucleic acid
       (C) STRANDEDNESS: unknown
       (D) TOPOLOGY: unknown (ii) MOLECULE TYPE: DNA (iii) HYPOTHETICAL: no (iv) ANTI-SENSE: yes (v) FRAGMENT TYPE:

(vi) ORIGINAL SOURCE:

(vii) IMMEDIATE SOURCE:

(viii) POSITION IN GENOME: CD44 991

(ix) FEATURE:

(x) PUBLICATION INFORMATION:

(xi) SEQUENCE DESCRIPTION: SEQ ID NO:2:

TTTATCTTCT TCCAAGGCGA AGC                                    23

(2) INFORMATION FOR SEQ ID NO:3:

(i) SEQUENCE CHARACTERISTICS:
       (A) LENGTH: 16 base pairs
       (B) TYPE: nucleic acid
       (C) STRANDEDNESS: unknown
       (D) TOPOLOGY: unknown (ii) MOLECULE TYPE: DNA

```
        (iii) HYPOTHETICAL: no (iv) ANTI-SENSE: yes (v) FRAGMENT TYPE:

(vi) ORIGINAL SOURCE:

(vii) IMMEDIATE SOURCE:

(viii) POSITION IN GENOME: CD44 991

(ix) FEATURE:

(x) PUBLICATION INFORMATION:

(xi) SEQUENCE DESCRIPTION: SEQ ID NO:3:

TTTATCTTCT TCCAAG                                                         16

(2) INFORMATION FOR SEQ ID NO:4:

(i) SEQUENCE CHARACTERISTICS:
              (A) LENGTH: 13 base pairs
              (B) TYPE: nucleic acid
              (C) STRANDEDNESS: unknown
              (D) TOPOLOGY: unknown (ii) MOLECULE TYPE: DNA (iii) HYPOTHETICAL: no (iv) ANTI-SENSE: yes (v) FRAGMENT TYPE:

(vi) ORIGINAL SOURCE:

(vii) IMMEDIATE SOURCE:

(viii) POSITION IN GENOME: CD44 2038

(ix) FEATURE:

(x) PUBLICATION INFORMATION:

(xi) SEQUENCE DESCRIPTION: SEQ ID NO:4:

TTCCTCCCAG GAC                                                            13

(2) INFORMATION FOR SEQ ID NO:5:

(i) SEQUENCE CHARACTERISTICS:
              (A) LENGTH: 14 base pairs
              (B) TYPE: nucleic acid
              (C) STRANDEDNESS: unknown
              (D) TOPOLOGY: unknown (ii) MOLECULE TYPE: DNA (iii) HYPOTHETICAL: no (iv) ANTI-SENSE: yes (v) FRAGMENT TYPE:

(vi) ORIGINAL SOURCE:

(vii) IMMEDIATE SOURCE:

(viii) POSITION IN GENOME: CD44 2038

(ix) FEATURE:

(x) PUBLICATION INFORMATION:

(xi) SEQUENCE DESCRIPTION: SEQ ID NO:5:
```

```
AAATTTCCTC CCAG                                                                  14

(2) INFORMATION FOR SEQ ID NO:6:

(i) SEQUENCE CHARACTERISTICS:
           (A) LENGTH: 15 base pairs
           (B) TYPE: nucleic acid
           (C) STRANDEDNESS: unknown
           (D) TOPOLOGY: unknown (ii) MOLECULE TYPE: DNA (iii) HYPOTHETICAL: no (iv) ANTI-SENSE: yes (v) FRAGMENT TYPE:

(vi) ORIGINAL SOURCE:

(vii) IMMEDIATE SOURCE:

(viii) POSITION IN GENOME: CD44 250

(ix) FEATURE:

(x) PUBLICATION INFORMATION:

(xi) SEQUENCE DESCRIPTION: SEQ ID NO:6:

GGCAGGTTAT ATTCA                                                                 15

(2) INFORMATION FOR SEQ ID NO:7:

(i) SEQUENCE CHARACTERISTICS:
           (A) LENGTH: 23 base pairs
           (B) TYPE: nucleic acid
           (C) STRANDEDNESS: unknown
           (D) TOPOLOGY: unknown (ii) MOLECULE TYPE: DNA (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME: CD44 250

(ix) FEATURE:

(x) PUBLICATION INFORMATION:

(xi) SEQUENCE DESCRIPTION: SEQ ID NO:7:

ATTTGAATAT AACCTGGCGA AGC                                                        23

(2) INFORMATION FOR SEQ ID NO:8:

(i) SEQUENCE CHARACTERISTICS:
           (A) LENGTH: 18 base pairs
           (B) TYPE: nucleic acid
           (C) STRANDEDNESS: unknown
           (D) TOPOLOGY: unknown (ii) MOLECULE TYPE: DNA (iii) HYPOTHETICAL: no (iv) ANTI-SENSE: no (v) FRAGMENT TYPE:
```

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION: SEQ ID NO:8:

TGCCAGACTA TTGTCCCA                                                          18

(2) INFORMATION FOR SEQ ID NO:9:

(i) SEQUENCE CHARACTERISTICS:
            (A) LENGTH: 26 base pairs
            (B) TYPE: nucleic acid
            (C) STRANDEDNESS: unknown
            (D) TOPOLOGY: unknown (ii) MOLECULE TYPE: DNA (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:CD44 520

(ix) FEATURE:

(x) PUBLICATION INFORMATION: Stamenkovic et al., The EMBO
            Journal, 1991, 10: 343-348.

(xi) SEQUENCE DESCRIPTION: SEQ ID NO:9:

GACACATATT GCTTCAATGC TTCAGC                                                 26

(2) INFORMATION FOR SEQ ID NO:10:

(i) SEQUENCE CHARACTERISTICS:
            (A) LENGTH: 29 base pairs
            (B) TYPE: nucleic acid
            (C) STRANDEDNESS: unknown
            (D) TOPOLOGY: unknown (ii) MOLECULE TYPE: DNA (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:CD44 920

(ix) FEATURE:

(x) PUBLICATION INFORMATION: Stamenkovic et al., The EMBO
            Journal, 1991, 10: 343-348.

(xi) SEQUENCE DESCRIPTION: SEQ ID NO:10:

GATGCCAAGA TGATCAGCCA TTCTGGAAT                                              29

(2) INFORMATION FOR SEQ ID NO:11:

(i) SEQUENCE CHARACTERISTICS:
        (A) LENGTH: 19 base pairs
        (B) TYPE: nucleic acid
        (C) STRANDEDNESS: unknown
        (D) TOPOLOGY: unknown (ii) MOLECULE TYPE: DNA (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:CD44 947

(ix) FEATURE:

(x) PUBLICATION INFORMATION: Stamenkovic et al., The EMBO
        Journal, 1991, 10: 343-348.

(xi) SEQUENCE DESCRIPTION: SEQ ID NO:11:

AGCAGAGTAA TTCTCAGAG                                    19

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:CD44 1221

(ix) FEATURE:

(x) PUBLICATION INFORMATION: Stamenkovic et al., The EMBO
        Journal, 1991, 10: 343-348.

(xi) SEQUENCE DESCRIPTION: SEQ ID NO:12:

CTGATAAGGA ACGATTGACA                                  20

(2) INFORMATION FOR SEQ ID NO:13:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (ii) MOLECULE TYPE: DNA (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:CD44 1221

(ix) FEATURE:

(x) PUBLICATION INFORMATION: Stamenkovic et al., The EMBO
             Journal, 1991, 10: 343-348.

(xi) SEQUENCE DESCRIPTION: SEQ ID NO:13:

GAGACCAAGA CACATTCCAC CCCAG                                                  25

(2) INFORMATION FOR SEQ ID NO:14:

(i) SEQUENCE CHARACTERISTICS:
             (A) LENGTH: 21 base pairs
             (B) TYPE: nucleic acid
             (C) STRANDEDNESS: unknown
             (D) TOPOLOGY: unknown (ii) MOLECULE TYPE: DNA (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:CD44 1221

(ix) FEATURE:

(x) PUBLICATION INFORMATION: Stamenkovic et al., The EMBO
             Journal, 1991, 10: 343-348.

(xi) SEQUENCE DESCRIPTION: SEQ ID NO:14:

ACTCCTTGTT CACCAAATGC A                                                      21

(2) INFORMATION FOR SEQ ID NO:15:

(i) SEQUENCE CHARACTERISTICS:
             (A) LENGTH: 21 base pairs
             (B) TYPE: nucleic acid
             (C) STRANDEDNESS: unknown
             (D) TOPOLOGY: unknown (ii) MOLECULE TYPE: DNA (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:CD44 182

(ix) FEATURE:

(x) PUBLICATION INFORMATION: Stamenkovic et al., The EMBO
             Journal, 1991, 10: 343-348.

(xi) SEQUENCE DESCRIPTION: SEQ ID NO:15:

ACACCTTGTT CACCAAATGC A                                                      21

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION: SEQ ID NO:16:

CTTCGAAAGG CAAGGAGGAA                                  20

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (iii) HYPOTHETICAL: no (iv) ANTI-SENSE: yes (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION: SEQ ID NO:17:

TGGCTCTACA ATCCTCAGCA                                  20

(2) INFORMATION FOR SEQ ID NO:18:

(i) SEQUENCE CHARACTERISTICS:
        (A) LENGTH: 23 base pairs
        (B) TYPE: nucleic acid
        (C) STRANDEDNESS: unknown
        (D) TOPOLOGY: unknown (ii) MOLECULE TYPE: DNA (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION: SEQ ID NO:18:

CAGCCATGTA CGTTGCTATC CAG                                                  23

(2) INFORMATION FOR SEQ ID NO:19:

(i) SEQUENCE CHARACTERISTICS:
              (A) LENGTH: 21 base pairs
              (B) TYPE: nucleic acid
              (C) STRANDEDNESS: unknown
              (D) TOPOLOGY: unknown (ii) MOLECULE TYPE: DNA (iii) HYPOTHETICAL: no (iv) ANTI-SENSE: yes (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION: SEQ ID NO:19:

GTTTCGTGGA TGCCACAGGA C                                                    21

(2) INFORMATION FOR SEQ ID NO:20:

(i) SEQUENCE CHARACTERISTICS:
              (A) LENGTH: 30 base pairs
              (B) TYPE: nucleic acid
              (C) STRANDEDNESS: unknown
              (D) TOPOLOGY: unknown (ii) MOLECULE TYPE: DNA (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION: SEQ ID NO:20:

CCTGAAGAAG ATTGTACATC AGTCACAGAC                                           30